United States Patent
Lugo et al.

(10) Patent No.: US 11,793,217 B1
(45) Date of Patent: Oct. 24, 2023

(54) METHOD OF MANUFACTURE AND PASTEURIZATION OF PRODUCTS CONTAINING UNDENATURED COLLAGEN

(71) Applicant: LONZA GREENWOOD LLC, Greenwood, SC (US)

(72) Inventors: James Patrick Lugo, Benicia, CA (US); Zainulabedin Mohamedali Saiyed, San Ramon, CA (US)

(73) Assignee: LONZA GREENWOOD LLC, Greenwood, SC (US)

( * ) Notice: Subject to any disclaimer, the term of this patent is extended or adjusted under 35 U.S.C. 154(b) by 286 days.

(21) Appl. No.: 15/724,220

(22) Filed: Oct. 3, 2017

Related U.S. Application Data

(60) Provisional application No. 62/404,065, filed on Oct. 4, 2016.

(51) Int. Cl.
*A23L 2/52* (2006.01)
*A23L 3/16* (2006.01)
*A61L 2/04* (2006.01)

(52) U.S. Cl.
CPC ... *A23L 2/52* (2013.01); *A23L 3/16* (2013.01); *A61L 2/04* (2013.01); *A23V 2002/00* (2013.01)

(58) Field of Classification Search
CPC .............. A23L 2/52; A23L 3/16; A61L 2/04; A23V 2250/5422
USPC .......................................... 426/590, 656, 520
See application file for complete search history.

(56) References Cited

U.S. PATENT DOCUMENTS

| | | | |
|---|---|---|---|
| 3,695,890 A * | 10/1972 | Miller | |
| 5,529,786 A | 6/1996 | Moore | |
| 5,570,144 A | 10/1996 | Lofgren-Nisser | |
| 5,637,321 A | 6/1997 | Moore | |
| 5,645,851 A | 7/1997 | Moore | |
| 7,083,820 B2 | 8/2006 | Schilling et al. | |
| 7,846,487 B2 | 12/2010 | Schilling et al. | |
| 9,066,926 B2 | 6/2015 | Dijkstra et al. | |
| 2010/0021600 A1* | 1/2010 | Yagi et al. | |
| 2011/0033606 A1* | 2/2011 | Ito et al. | |
| 2013/0020713 A1* | 1/2013 | Premachandran et al. | |
| 2013/0207130 A1* | 8/2013 | Reiherzer et al. | |
| 2015/0017129 A1* | 1/2015 | Moore | |

FOREIGN PATENT DOCUMENTS

CN          104,161,287      * 11/2014

OTHER PUBLICATIONS

Cao et al., "Purification and characterization of type II collagen from chick sternal cartilage," Food Chemistry 108: 439-445 (2008).
Ignat'eva et al., "Effect of Supramolecular Organization of a Cartilaginous Tissue on Thermal Stability of Collagen II," Russian Journal of Physical Chemistry, Vol. 80, pp. 1336-1341 (2006).
Logunova et al., "Decreased Collagen Thermal Stability as a Response to the Loss of Structural Integrity of Thyroid Cartilage," Biophysics, Vol. 53, No. 5:470-475 (2008).
Than et al., "Thermal Analysis of the Osteoarthritic Human Hyaline Cartilage," Journal of Thermal Analysis and Calorimetry, Vol. 82, 213-216 (2005).

* cited by examiner

*Primary Examiner* — Helen F Heggestad
(74) *Attorney, Agent, or Firm* — MARSHALL, GERSTEIN & BORUN LLP

(57) ABSTRACT

The present invention provides a method of heat treating undenatured collagen to reduce microbial load comprising the subjection of said collagen to a temperature of at least 40° C. for a time of at least 2 seconds in a manner sufficient to reduce microbial content without denaturing more than 20% of the collagen protein.

22 Claims, 1 Drawing Sheet

METHOD OF MANUFACTURE AND PASTEURIZATION OF PRODUCTS CONTAINING UNDENATURED COLLAGEN

BACKGROUND OF THE INVENTION

The present invention relates to methods for the manufacture of undenatured collagen at elevated temperatures, which may be used in nutritional supplements and health care formulations.

In particular, the invention relates to methods of reducing the microbial content of undenatured Type II collagen which is particularly useful in the treatment of arthritic and non-arthritic medical conditions in humans and other mammals, for example joint pain.

Of interest to the present application are the disclosures of Moore U.S. Pat. Nos. 5,570,144, 5,529,786, 5,637,321 and 5,645,851 which are directed to the administration of chicken derived Type II collagen for the treatment of Rheumatoid Arthritis and Osteoarthritis. In addition, Dijkstra et al., U.S. Pat. No. 9,066,926 discloses a method of treating exercise and mechanically induced joint pain in arthritis-free mammals by the administration of Type II collagen (collagen II).

It has further been observed that it is important that the Type II collagen be undenatured (e.g., its native, or natural, conformation) in order to be useful in treating arthritic and non-arthritic conditions. Such an undenatured conformation is best analyzed by means of enzyme linked immunosorbent assay (ELISA) methods, which utilize monoclonal or polyclonal antibodies to detect and to quantify the presence of the undenatured collagen molecule.

Also of interest to the present invention are the disclosures of Schilling, U.S. Pat. Nos. 7,083,820 and 7,846,487 which are directed to methods for producing undenatured Type II collagen which retains the collagen II in its original crosslinked, insoluble structure in a dehydrated, stabilized form. The Schilling patents disclose products of a process which comprises the dehydration and thus stabilization of the avian articular cartilage at less than traditional processing temperatures and in the presence of an ionizable salt that is not harmful to the consumer in the concentrations employed. According to one aspect of the Schilling patents, chicken sternal cartilage is obtained from young chickens and treated with an antimicrobial agent such as a hypochlorite, a nitrate or nitrite before being ground to an average particle size of 0.25" (6 mm) and being dried in a fluid bed reactor to reduce the water content by about 50%. The dried comminuted chicken cartilage is then mixed with an ionizable salt, such as potassium chloride, and is dried with particular attention being paid to ensure that the temperature of the resulting product does not exceed 110° F. (43° C.) until the water content is below 2%. It is believed that the salt stabilizes the native collagen II protein in the articular cartilage against hydrolysis and degeneration of the crosslinked structure. Nevertheless, the Schilling patents teach that fresh chicken sternal cartilage subjected to thermal processing at 250° F. (121° C.) for one hour contained less than 1% "almost unmeasurable" amounts of crosslinked (undenatured) collagen II after said treatment.

During and after processing, the salt also acts as an antimicrobial stabilizer against the growth of pathogens and spoilage organisms both during the manufacturing process, which is oftentimes set at temperatures conducive for the growth of the aforementioned organisms, as well as during the extended storage of said product. While the presence of such salt is believed to reduce the microbial content of the composition over time, the curing process can be very time consuming requiring extended treatment to reduce the microbial load to within desired limits. Accordingly, there remains a desire to identify further methods by which the microbial content of collagen compositions can be reduced or substantially or completely eliminated in a relatively rapid manner without having a deleterious effect on the biological activity of the composition due to the denaturation of the collagen II active ingredient.

Common methods for reducing the microbial content of food and other consumable ingredients is heat treatment (such as cooking), treatments with chemicals such as acids, alkalis and the like. Nevertheless, there is a desire to avoid "cooking" the source material because of the likelihood of denaturing the constituent collagen (s). Moreover, there is a desire to avoid chemical treatment of foods and other consumables. Even if the chemical treatment is as simple as acid or alkali treatment there is a similar desire to avoid such treatment because of concerns that such treatment will negatively affect the utility of the resulting composition such as by denaturing the protein structure of the collagen.

Pasteurization is the method invented by Louis Pasteur in the 19th century by which spoilage of beverages such as milk, fruit juices, and wine could be reduced by the application of heat to reduce their microbial contents. Pasteurization is distinguished from sterilization, which is intended to kill all the micro-organisms. Sterilization is not commonly practiced with food and beverage products because of adverse effects on taste and quality of the food and beverage. Similarly, pasteurization can affect qualities of the food but in more minor ways. For example, pasteurization is known to denature dairy proteins such as casein and whey but does not affect the nutritional quality of the treated milk. Different protocols for pasteurization are practiced for different products destined for different uses or having different intended storage times. Low-temperature, long-time (LTLT) pasteurization of milk heats the milk to 63° C. for at least 30 minutes and produces a product which is shelf stable upon delivery to the consumer for up to six days. High-temperature, short-time (HTST) pasteurization of milk heats milk to 72° C. for 15 seconds and provides a product which remains stable under refrigeration after delivery to the consumer for five to 15 days. Ultra-heat treating (UHT) treats the milk at a temperature of 140° C. for four seconds and essentially sterilizes the milk such that it may be stored for several months without refrigeration. Each of these processes denatures some of the milk proteins (casein and whey) to varying degrees with UHT treated milk being unsuitable for manufacture of cheese.

Not only does there exist an ongoing concern regarding the possibility of infection resulting from uncooked or undercooked food products but a similar concern also exists from the use of animal sources for food and nutraceutical ingredients where those animal sources are not cooked or subjected to sterilization procedures prior to extraction of ingredients ultimately intended for human and other mammalian consumption.

Accordingly, there remains a desire in the art to identify methods for reducing the microbial content of collagen compositions extracted from uncooked, unsterilized animal sources such as chickens, cows, pigs, fish and other animals. As used herein "microbial" is intended to encompass bacterial, fungal (including yeasts) and viral contaminants that are undesired in a product for human or non-human mammal consumption.

Of interest to the present invention is the finding of Cao et al., Food Chemistry 108: 439-445 (2008) which discloses the purification of Type II collagen from chick sternal cartilage using a combination of pepsin digestion, NaCl precipitation and DEAE-sepharose ion exchange chromatography. Both purified and matrix bound collagen (i.e., intact sternal cartilage) were heated according to a protocol whereby the sample temperature was increased by 5° C. each minute and the denaturation temperature was determined to be 44° C. for both materials, using differential scanning calorimetry (DSC) which measures phase changes in the heated samples. Such results indicate that the presence of collagen in a sternal or other biological matrix does not impact the temperature at which this protein denatures.

Also of interest to the present invention is the disclosure of Than et al., J. Thermal Analysis and Calorimetry Vol. 82, 213-216 (2005) which described a thermal analysis of osteoarthritic human hyaline cartilage which reported an endothermic reaction at around 60° C.

Ignat'eva et al., Russian, J. Phys. Chem Vol 80, No. 8 1336-1341 (2006) reported on the thermal stability of collagen II in various cartilaginous tissues including nucleus pulposus (vertebral disc) showing melting within a temperature range of 60-70° C. and hyaline cartilage of nasal septum and cartilage endplates which was said to be not denatured completely up to 100° C.

Also of interest to the present invention is the disclosure of Logunova et al., Biophysics Vol 53, No. 5:470-475 which provides other DSC data regarding collagen thermal stability. While perichondrium derived cartilage was reported to have a melting (denaturation) temperature of 65° C., the hyaline constituent of collagen was indicated to not denature at temperatures up to 100° C. Of significance to the present invention is the fact that while DSC analysis measures endothermic and exothermic transitions in the analyzed materials, which can be indicative of phase changes, it does not necessarily measure the biological activity or conformational structures of each component of a complex sample matrix containing multiple biological materials, including proteins. As such, DSC may not measure subtle variations in protein structure that can result in changes in biological activity. This limitation would not apply to mixtures containing a single component protein, but may when the complex sample contains multiple proteins, proteoglycans and other constituents as is generally the case with tissues such as the sternal cartilage.

There remains a desire in the art to develop methods for reducing the microbial content of collagen compositions without denaturing the collagen and thereby preserve the biological activity of the collagen.

SUMMARY OF THE INVENTION

The present invention relates to the surprising finding that undenatured collagen compositions can be heated for extended time periods at elevated temperatures without significant denaturing of the collagen protein. The unexpected finding that matrix bound proteins, such as collagen embedded in chicken sternum, maintain their native conformational structure at high temperatures makes it possible to reduce the microbial content of various collagen containing biological products without denaturing the collagen protein. More specifically, the invention provides methods of manufacturing undenatured collagen under heat treatment conditions capable of reducing the microbial load comprising subjecting said collagen composition to a temperature of at least 40° C. for a time of at least 2 seconds in a manner to reduce microbial contamination without denaturing the collagen protein by more than 10%. As provided herein the extent of collagen protein denaturation is determined by the use of a specific antibody ELISA method that binds to the undenatured form of collagen. Such a method is in contrast to thermoanalytical techniques such as differential scanning calorimetry (DSC) that relies on physical transformation and phase transitions, which may not accurately determine the in situ biophysical state of the collagen proteins (e.g., native versus denatured) in the matrix.

According to preferred methods, prepared undenatured collagen protein not subjected to heat treatment, is less denatured than collagen preparations subjected to heat treatment. However, following the application of said heat treatment no more than 5% or 3% or 1% of the original undenatured collagen preparation is expected to be denatured.

It is further contemplated that the heat treating method may be carried out at various combinations of temperatures and times as disclosed herein and as would be appreciated by one of ordinary skill in the art when apprised by the data provided herein. Thus, the heating can be carried out at temperatures of at least 50° C., or at least 60° C., or at least 70° C., or at least 80° C., or at least 90° C., or at least 100° C., or at least 110° C., or at least 120° C., or at least 130° C., or at least 140° C., or at least 150° C., or at least 160° C., or at least 170° C., or at least 180° C., or at least 190° C., or at least 200° C. or greater, for at least 2 seconds and more preferably 30 seconds, or 1 minute. The heating may also be carried out for 3 minutes or 5 minute or 10 minutes or 15 minutes but may also be carried out for other time periods such as 20 minutes, 30 minutes or 60 minutes or longer. As a further aspect of the invention it is contemplated that heating to reduce the microbial content of the composition may be carried out without reducing the content of undenatured collagen by greater than 10% at higher temperatures such as at least 90° C., or at least 100° C., or at least 110° C., or at least 120° C., or at least 130° C., or at least 140° C., or at least 150° C., or at least 160° C., or at least 170° C., or at least 180° C., or at least 190° C., or at least 200° C. or greater, for time periods of at least 2 seconds to 10 minutes, or 10 minutes to 20 minutes or longer up to one hour. According to a particularly preferred aspect of the invention the heating is carried out at 120° C. for 30 minutes or 60 minutes or for a time in between and is effective to substantially diminish the microbial load of the collagen composition while maintaining a substantial portion of the collagen in an undenatured state. It is further contemplated that the heat treatment may be carried out in a liquid, such a water and can also be carried out at pressures greater than atmospheric such as in an autoclave which can allow for higher heating temperatures.

The heat treatments may be carried out in a dry oven having a relative humidity of less than 10%. Alternatively, the heating may also be carried out at elevated relative humidity levels of at least 20% or at least 30%, or greater.

In an additional embodiment of the invention, it is further contemplated that the heat treatment be carried out in the presence of an ionizable salt which can be any of a variety of such salts but which is preferably selected from the group of ingestible salts consisting of sodium chloride and potassium chloride.

According to one aspect of the invention collagen containing sternal material can be heated in boiling water for time periods of up to 5 minutes, or up to 10 minutes or up to 15 minutes to provide a starting material free of microbial contamination from which undenatured collagen can be isolated according to methods known in the art and described below.

According to one aspect of the invention, the collagen is produced by a method comprising a shearing step in which the collagen containing cartilage is comminuted to an average particle size of less than 15 mm and more preferably less than 10 mm and according to one embodiment has an average particle size of about 6 mm. Such collagen compositions can be produced using methods which include shearing, slicing, chopping and other mechanically disruptive steps.

The methods of the invention may be carried out using any type of collagen including particularly fibrillar type collagens including Type I, Type II, Type III and Type V and Type XI collagen. In particularly the invention is directed to preparation and manufacture of Type II collagen compositions which are particularly useful for treatment of arthritis and non-arthritis conditions in humans and other mammals. Use of collagen derived from all mammalian and non-mammalian species is contemplated by the invention but preferred sources of undenatured Type II collagen are bovine, fish and porcine derived collagen with avian derived collagen and particularly chicken sternum derived collagen being typically used. Other sources of undenatured Type-II collagen may be used without departing from the present invention.

While collagen compositions have customarily been delivered in a dry format, such as in tablets or capsules, the methods of the invention may also be used to simplify the production of beverages containing an undenatured collagen component. According to this aspect of the invention, the undenatured collagen component need not be treated for microbial contamination before being combined with the other beverage components. Instead, the undenatured collagen component may be combined with the other beverage components and the entire combination subjected to a heating step so as to reduce microbial contamination and sealed as part of the "bottling" process. Such a heating step would pasteurize the entire product without denaturing substantial amounts of the collagen. Alternatively, the undenatured collagen component, once heat treated, can be added to beverages, dairy products, and other food items or formulations (e.g., gummies, quick dissolve oral strips, chocolates, soft chews, etc.) previously heat treated, without compromising the overall safety of the beverage or the food item.

Also provided by the invention are undenatured collagen products having a reduced microbial content produced according to heat treating methods described above and particularly those that comprise undenatured Type II collagen.

DETAILED DESCRIPTION

Figure 1:
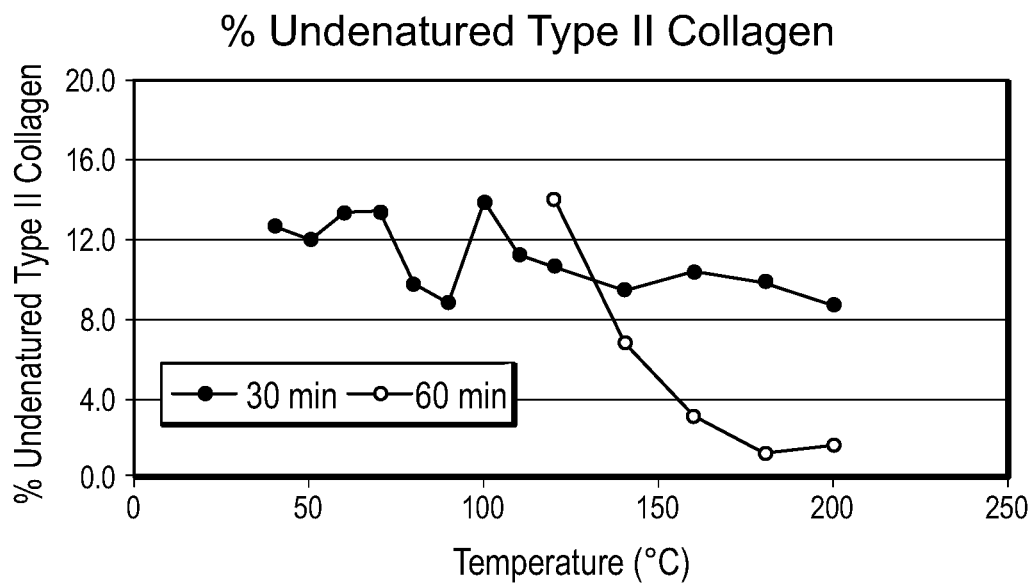
FIG. 1 depicts the percentage of undenatured Type II collagen when treated at various temperatures for either 30 minutes or 60 minutes.

The present invention relates to the surprising finding that undenatured collagen compositions can be heated for extended time periods at elevated temperatures in order to reduce their microbial content without denaturing the collagen protein. The sources of collagen are described above and include bovine, porcine, avian, and fish. Of particular importance is avian collagen, in particular chicken sternums. More specifically the invention provides methods of heat treating undenatured collagen to reduce microbial contamination comprising subjecting said collagen to a temperature of greater than 40° C. for a time period sufficient to reduce microbial contamination without denaturing more than 10% of the collagen protein. Without intending to be bound by any particular theory of the invention it is hypothesized that the matrix (sternum) from which the Type II collagen is derived may act as a "crystallizing" milieu that keeps the type II collagen from unfolding thereby making it highly resistant to heat denaturation. This is a surprising result sin As used herein, a reduction in microbial content is contemplated to mean a 50% reduction in microbial content such as by counting colony forming units but is preferably contemplated to mean a 10-fold reduction in microbial content. It is recognized that good hygienic practices will usually produce collagen products having minimal microbial contamination. Nevertheless, because of the catastrophic consequences of even a very few or only one contaminated product reaching consumers, the present invention is intended to treat many uncontaminated products in order to ensure product safety.

Undenatured collagen to which the methods of the invention may be applied includes that isolated by any of the various methods known to the art including
1. Receiving of raw chicken sternums;
2. Optionally washing the sternums with antimicrobial agent(s), as required;
3. Drying of the sternal cartilage at temperatures below 40° C.;
4. Grinding the dry cartilage;
5. Milling the blend to a desired particle size.

Alternatively, the drying of the sternal cartilage could take place above 40° C., in accordance with the present invention.

Alternatively, undenatured collagen to which the methods of the invention may be applied includes that isolated by any of the various methods known to the art including those described in any of Moore U.S. Pat. Nos. 5,570,144, 5,529,786, 5,637,321 and 5,645,851 or of Schilling, U.S. Pat. Nos. 7,083,820 and 7,846,487, each hereby incorporated by reference in its entirety. Those of ordinary skill in the art would appreciate that such undenatured collagen can be isolated according to a method comprising the steps of
1. Receiving of raw chicken sternums;
2. Washing the sternums with antimicrobial agent(s) as required;
3. Drying of the sternal cartilage at temperatures below 40° C.;
4. Grinding the dry cartilage;
5. Adding ionizable salt (KCl or NaCl or others) to the ground cartilage;
6. Re-grinding and blending of salt with the ground cartilage;
7. Drying the blend;
8. Milling the blend to a desired particle size.

According to one aspect of the invention it is desired that the process does not involve use of any proteolytic enzymes or cartilage matrix degrading enzymes so as to protect the native structure of Type II collagen.

In the process of the present invention, undenatured collagen containing cartilage is subject to heat treatment conditions capable of reducing the microbial load comprising. The heat treatment included heating of the collagen composition to a temperature of at least 40° C. for a time of at least 2 seconds in a manner to reduce microbial content without denaturing more than 20% of the collagen protein. The heat treatment may be carried out at temperatures of at least 40° C. or higher. For example the heat treatment may be at a temperature of at least 50° C., or at least 60° C., or at least 70° C., or at least 80° C., or at least 90° C., or at least 100° C., or at least 110° C., or at least 120° C., or at least 130° C., or at least 140° C., or at least 150° C., or at least 160° C., or at least 170° C., or at least 180° C., or at least 190° C., or at least 200° C. or greater. The heat treatment may take place for a short as a few seconds up to several minutes. For example, the heat treatment may be for at least 2 seconds, typically at least 10 seconds or long, such as 30 seconds, or 1 minute. The heating may also be carried out for longer periods of time, such as 90 seconds, 2 minute 3 minutes or 5 minute or 10 minutes or 15 minutes. Longer periods of time may also be used, such as 20 minutes, 30 minutes or 60 minutes or longer. The period of time used can be determined based on the collagen source, or the process conditions used to manufacture the undenatured collagen. Generally, the temperature should not exceed 250° C. and the time should not exceed 120 minutes. The temperature and time used should be selected so as not to cause more than 20% of the collagen protein to become denatured. Ideally, not more than 10% of the collagen protein to become denatured, and typically not more than 5% of the collagen protein to become denatured using the process of the present invention.

It is further preferred that ionizable salt be blended with the product because it provides stability to the undenatured Type II collagen so that it can retain its native protein structure even when subjected to high temperatures and humidity for various time intervals. The ionizable salt is added to the undenatured Type II collagen containing cartilage in an amount of at least 1% by weight, prior to heat treating or drying. Typically, the ionizable salt is added in an amount of at least 5% by weight, and more typically at least 15% by weight of the undenatured Type II collagen containing cartilage. The ionizable salt should be consumable by mammals. Suitable salts include, for example, sodium or potassium chloride. Other salts that are consumable by mammals may also be used. Salt concentrations vary widely depending on the nature of the food material involved and the degree of stabilization desired.

According to one aspect of the invention it is particularly surprising that heat treatment is capable of reducing microbial content with minimal denaturation of the collagen protein where the collagen containing material was ground, chopped or otherwise physically comminuted such as to produce fragments having particle sizes of less than 15 mm and less than 10 mm in size because such physical treatment might render the collagen triple helix more susceptible to denaturation at lower temperatures and times due to the destruction (i.e., destabilization) of the complex proteoglycan matrix enveloping the collagen protein.

Example 1

According to this example undenatured Type II collagen was subjected to heating at specified temperatures and times to determine the ability to reduce the microbial content of the sample and whether such treatment denatured the collagen as measured by ELISA.

The results presented in Table 1 below show that heating sample of undenatured Type-II collagen (≤10% moisture content) in an oven for 15 minutes acted to reduce the total mold count at various temperatures but did not destroy (e.g., denature) the tertiary structure of the undenatured Type II collagen at temperatures as high as 90° C. (dry heat). Because the samples treated were generally free of other microbial contaminants additional testing is contemplated which will demonstrate the efficacy of such heat treatment in reducing other microbial contamination while also failing to denature the Type II collagen under other time, temperature and moisture conditions.

TABLE 1

| Sample | 1 | 2 | 3 | 4 | 5 | 6 | 7 |
| --- | --- | --- | --- | --- | --- | --- | --- |
| Incubation temp. (°C. dry heat in oven) | Preincubation | 40 | 50 | 60 | 70 | 80 | 90 |
| Incubation time (min) | - | | | | 15 | | |
| Results | | | | | | | |
| Undenatured type II collagen (by IH validated ELISA) | 10.6% | 10.2% | 9.16% | 10.6% | 11.4% | 11.8% | 9.56% |
| Total Aerobic microbial count (CFU/g) (by USP 2021) | <10 | <10 | <10 | <10 | <10 | <10 | <10 |
| Total mold count (CFU/g) (by USP 2021) | 20 | <10 | <10 | <10 | <10 | <10 | <10 |
| Total yeast count (CFU/g) (by USP 2021) | <10 | <10 | <10 | <10 | <10 | <10 | <10 |
| Escherichia coli (by USP 2022) | Neg. | Neg. | Neg. | Neg. | Neg. | Neg. | Neg. |
| Salmonella (by USP 2022) | Neg. | Neg. | Neg. | Neg. | Neg. | Neg. | Neg. |
| Staphylococcus aureus (by USP 2022) | Neg. | Neg. | Neg. | Neg. | Neg. | Neg. | Neg. |

Example 2

According to this example undenatured Type II collagen was subjected to heating at specified temperatures and times to determine the ability to reduce the microbial content of the sample and whether such treatment denatured the collagen as measured by ELISA.

Figure 2:
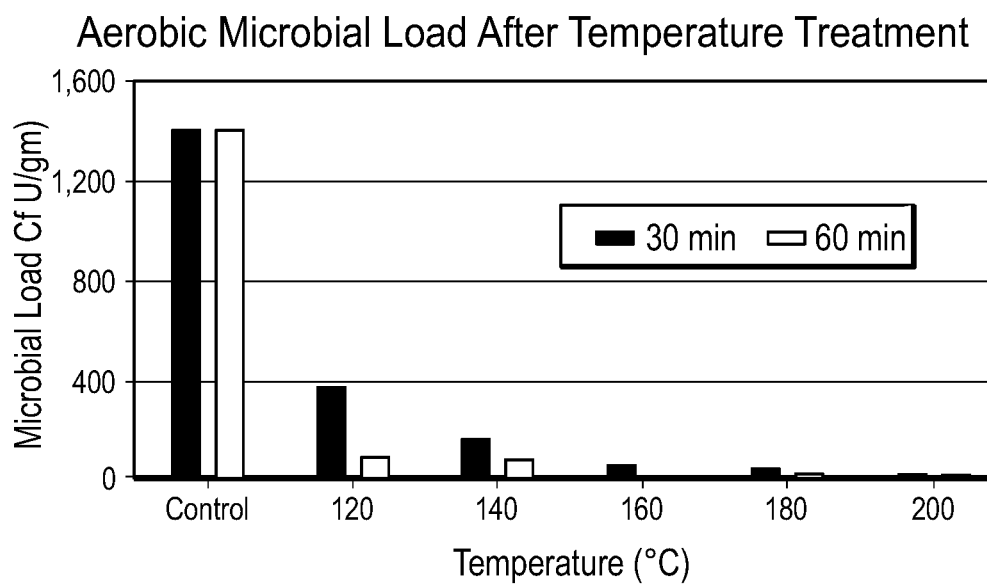
FIG. 2 depicts the microbial load in a Type II collagen composition when treated at various temperatures for either 30 minutes or 60 minutes.

The results shown in FIGS. 1 and 2 show the percentage of undenatured Type II collagen when treated at various temperatures for either 30 minutes or 60 minutes (FIG. 1) as well as the microbial load after such high temperature treatment (FIG. 2) compared with a control. These results show that undenatured Type II collagen is stable from 40° C. to 200° C. when heated for 30 minutes or less (see FIG. 1). At temperatures of 120° C. and higher, the endogenous aerobic count of UC-II are reduced to 10-100 cfu per gram (starting plate count = 1400 cfu/gm). At temperatures beyond 120° C., 60 minute treatments start to significantly reduce the percentage of Type II collagen which remains undenatured. By 200° C., very little undenatured Type II collagen remains when treated for 60 minutes.

The results also showed that treatment for 30 minutes to 60 minutes at 120° C. will diminish the endogenous (aerobic) microbial load of the Type II collagen. At temperatures of 120° C. and above, all Bacillus cereus and Salmonella strains (typhimurium and heidelberg) are killed to 5 logs. Other experiments established that S. typhimurium can be killed to 6 logs after treatment at 110° C. for 30 minutes.

These results suggest that treatment at 120° C. for 30 minutes to 60 minutes may be preferred for commercial production.

Shown below in Table 2 below are analyses of Type II collagen products subjected to heating at 120° C. for 30 minutes and 60 minutes and compared to untreated such as for purposes of regulatory approval requiring a demonstration that high temperature baking or cooking of an ingredient causes only minor loss of volatile components and no other changes to the chemical or molecular composition or structure of the ingredient.

TABLE 2

| Chemical Parameter | Untreated | 120° C. 30 min | 120° C. 60 min |
|---|---|---|---|
| Carbohydrate, total (%) | 12.2 | 12.9 | 12.3 |
| Fat (%) | 0.94 | 0.84 | 0.87 |
| Loss on Drying (%) | 5.18 | 4.85 | 4.46 |
| Protein (%) | 44.5 | 44.3 | 45.0 |
| Protein Factor | 6.25 | 6.25 | 6.25 |
| Ash (%) | 37.2 | 37.1 | 37.4 |
| Chondroitin Sulfate (mg/g) | 89.6 | 90.6 | 82.3 |
| Collagen (mg/g) | 294 | 266 | 296 |
| Total Collagen (mg/g) | 36.7 | 33.3 | 37.0 |
| Undenatured Collagen (%)* | 10.0 | 10.6 | 14.1 |

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of manufacturing undenatured Type II collagen composition under heat treatment conditions comprising,
   a. providing raw chicken sternums containing sternal cartilage;
   b. washing the sternums with an antimicrobial agent(s);
   c. drying of the sternal cartilage at temperatures above 50° C. for a time of at least 2 seconds to form a dry cartilage;
   d. Grinding the dry cartilage to form a ground cartilage;
   e. Milling the ground cartilage to a desired particle size;
   wherein the method reduces the microbial content without denaturing more than 20% of the undenatured Type-II collagen in the collagen composition.

2. The method of claim 1, wherein no more that 10% of the Type-II collagen is denatured.

3. The method of claim 2, wherein no more than 5% of the Type-II collagen is denatured.

4. The method of claim 1 wherein the drying is at a temperature of at least 70° C.

5. The method of claim 1 wherein the collagen is treated for at least 60 seconds.

6. The method of claim 1 wherein the collagen is treated for at least 15 minutes.

7. The method of claim 1 wherein the collagen is treated at a relative humidity of less than 10%.

8. The method of claim 1 wherein the collagen is treated at a relative humidity of at least 20%.

9. The method of claim 1 wherein the collagen is treated at a relative humidity of at least 30% or greater.

10. The method of claim 1 wherein the heat treatment takes place in the presence of an ionizable salt.

11. The method of claim 1 wherein the collagen is produced by a method comprising a shearing, slicing, chopping, or other mechanically disruptive step in which the collagen containing cartilage is comminuted to an average particle size of less than 10 mm.

12. An undenatured Type II collagen product produced according to the method of claim 1.

13. The method of claim 1, further comprising adding an ionizable salt to the ground cartilage and re-grinding and blending the ionizable salt with the ground cartilage to form a blend.

14. The method of claim 13, further comprising drying the blend, wherein the drying blend is at temperatures above 50° C. for a time of at least 2 seconds, forming a dry blend.

15. The method of claim 14, wherein the milling of the dry cartilage comprises milling the dry blend.

16. The method of claim 15, wherein drying the blend is at a temperature of at least 70° C.

17. The method of claim 16, wherein drying the blend is at a temperature of at least 90° C.

18. The method of claim 17, wherein drying the blend is at a temperature of at least 110° C.

19. An undenatured Type II collagen product produced according to the method of claim 13.

20. An undenatured Type II collagen product produced according to the method of claim 14.

21. An undenatured Type II collagen product produced according to the method of claim 15.

22. An undenatured Type II collagen product produced according to the method of claim 16.

* * * * *